(12) United States Patent
Kurtz et al.

(10) Patent No.: US 11,027,154 B2
(45) Date of Patent: *Jun. 8, 2021

(54) ULTRASONIC THERAPY APPLICATOR AND METHOD OF DETERMINING POSITION OF ULTRASONIC TRANSDUCERS

(71) Applicant: Profound Medical Inc., Mississauga (CA)

(72) Inventors: Ron Kurtz, Oakville (CA); Cameron Mahon, Georgetown (CA); Sean Donaldson, Toronto (CA)

(73) Assignee: Profound Medical Inc., Mississauga (CA)

( * ) Notice: Subject to any disclaimer, the term of this patent is extended or adjusted under 35 U.S.C. 154(b) by 1018 days.

This patent is subject to a terminal disclaimer.

(21) Appl. No.: 15/621,672

(22) Filed: Jun. 13, 2017

(65) Prior Publication Data

US 2017/0304656 A1    Oct. 26, 2017

Related U.S. Application Data

(63) Continuation-in-part of application No. 12/932,920, filed on Mar. 9, 2011, now Pat. No. 9,707,413.
(Continued)

(51) Int. Cl.
*A61N 7/02* (2006.01)
*A61B 18/00* (2006.01)
(Continued)

(52) U.S. Cl.
CPC .... *A61N 7/022* (2013.01); *A61B 2018/00023* (2013.01); *A61B 2018/00202* (2013.01);
(Continued)

(58) Field of Classification Search
CPC .. A61N 7/022; A61N 7/02; A61N 2007/0091; A61N 2007/0078;
(Continued)

(56) References Cited

U.S. PATENT DOCUMENTS 4,326,418 A    4/1982 Pell, Jr.
4,880,011 A    11/1989 Imade et al.
(Continued)

FOREIGN PATENT DOCUMENTS

WO    WO2011045695 A1    4/2011
WO    WO2011091847 A1    8/2011

OTHER PUBLICATIONS

Chopra et al., Med. Phys., 27(6): 1281-1286, 2000.
(Continued)

*Primary Examiner* — Angela M Hoffa
*Assistant Examiner* — Helene Bor
(74) *Attorney, Agent, or Firm* — Intrinsic Law Corp.

(57) ABSTRACT

An apparatus is disclosed for thermal therapy in a male prostate patient. The apparatus includes a long tubular element that is to be inserted into a patient's urethra so that a first tip end of it reaches up into the patient's diseased prostate. The elongated portion includes a narrow cylindrical tube within which an ultrasonic array is disposed along the long axis of the cylinder. Fluid is pumped into and out of a treatment zone of said patient as needed to control a temperature of a region in said treatment zone. A motorized driver is used to controllably rotate said elongated portion and the ultrasound array therein about the long axis of the apparatus so as to deliver acoustic energy to said diseased tissue. Various control and monitoring components may be used in conjunction with the present apparatus to design, control, and terminate the therapy.

14 Claims, 15 Drawing Sheets

Related U.S. Application Data

(60) Provisional application No. 61/311,853, filed on Mar. 9, 2010.

(51) Int. Cl.
*A61N 7/00* (2006.01)
*A61B 90/00* (2016.01)
*A61B 34/20* (2016.01)

(52) U.S. Cl.
CPC ........... *A61B 2018/00517* (2013.01); *A61B 2018/00547* (2013.01); *A61B 2034/2051* (2016.02); *A61B 2090/067* (2016.02); *A61B 2090/363* (2016.02); *A61B 2090/374* (2016.02); *A61B 2090/378* (2016.02); *A61B 2090/3925* (2016.02); *A61B 2090/3937* (2016.02); *A61B 2090/3954* (2016.02); *A61N 2007/0078* (2013.01); *A61N 2007/0091* (2013.01)

(58) Field of Classification Search
CPC ........... A61B 18/1485; A61B 18/1815; A61B 2018/00547; A61B 2017/00274; A61B 2018/00517; A61B 2090/378; A61B 2018/00011; A61B 2090/374; A61B 2018/00023; A61B 2007/0091; A61B 2007/0078
See application file for complete search history.

(56) References Cited

U.S. PATENT DOCUMENTS

| | | |
|---|---|---|
| 5,295,484 A | 3/1994 | Marcus et al. |
| 5,593,381 A | 1/1997 | Tannenbaum et al. |
| 5,593,415 A | 1/1997 | Adrian |
| 5,601,526 A | 2/1997 | Chapelon et al. |
| 5,620,479 A | 4/1997 | Diederich |
| 5,647,361 A | 7/1997 | Damadian |
| 5,666,954 A | 9/1997 | Chapelon et al. |
| 5,733,315 A | 3/1998 | Burdette et al. |
| 6,007,257 A | 12/1999 | Ogawa et al. |
| 6,050,943 A | 4/2000 | Stayton et al. |
| 6,100,626 A | 8/2000 | Frey et al. |
| 6,113,546 A * | 9/2000 | Suorsa ............ A61B 8/4494 600/437 |
| 6,122,551 A | 9/2000 | Rudie et al. |
| 6,231,811 B1 * | 5/2001 | Namerikawa ........ G01N 29/02 310/328 |
| 6,241,725 B1 | 6/2001 | Cosman |
| 6,254,553 B1 | 7/2001 | Lidgren et al. |
| 6,379,320 B1 | 4/2002 | Lafon et al. |
| 6,393,314 B1 | 5/2002 | Watkins et al. |
| 6,418,337 B1 | 7/2002 | Torchia et al. |
| 6,432,067 B1 | 8/2002 | Martin et al. |
| 6,440,126 B1 * | 8/2002 | Abboud ............ A61B 18/02 606/21 |
| 6,490,488 B1 | 12/2002 | Rudie et al. |
| 6,500,121 B1 | 12/2002 | Stayton et al. |
| 6,516,211 B1 | 2/2003 | Acker et al. |
| 6,522,142 B1 | 2/2003 | Freundlich |
| 6,537,306 B1 | 3/2003 | Burdette et al. |
| 6,542,767 B1 | 4/2003 | McNichols et al. |
| 6,559,644 B2 | 5/2003 | Freundlich et al. |
| 6,582,381 B1 | 6/2003 | Yehezkeli et al. |
| 6,589,174 B1 | 7/2003 | Chopra et al. |
| 6,618,608 B1 | 9/2003 | Watkins et al. |
| 6,618,620 B1 | 9/2003 | Freundlich et al. |
| 6,623,430 B1 | 9/2003 | Stayton et al. |
| 6,671,535 B1 | 12/2003 | McNichols et al. |
| 6,692,450 B1 | 2/2004 | Coleman |
| 6,692,518 B2 | 2/2004 | Carson |
| 6,735,461 B2 | 5/2004 | Vitek et al. |
| 6,746,465 B2 | 6/2004 | Diederich et al. |
| 6,755,849 B1 | 6/2004 | Gowda et al. |
| 6,818,012 B2 | 11/2004 | Ellingboe |
| 6,823,216 B1 | 11/2004 | Salomir et al. |
| 7,044,960 B2 | 5/2006 | Voorhees et al. |
| 7,135,029 B2 | 11/2006 | Makin et al. |
| 7,167,741 B2 | 1/2007 | Torchia et al. |
| 7,229,411 B2 | 6/2007 | Stayton et al. |
| 7,233,820 B2 | 6/2007 | Gilboa |
| 7,344,529 B2 | 3/2008 | Torchia et al. |
| 7,404,809 B2 | 7/2008 | Susi |
| 7,473,224 B2 | 1/2009 | Makin |
| 7,771,418 B2 | 8/2010 | Chopra et al. |
| 7,806,892 B2 | 10/2010 | Makin et al. |
| 7,951,182 B2 | 5/2011 | Stelea et al. |
| 7,993,289 B2 | 8/2011 | Quistgaard et al. |
| 8,021,406 B2 | 9/2011 | Cazzini et al. |
| 8,025,688 B2 | 9/2011 | Diederich et al. |
| 8,066,641 B2 | 11/2011 | Barthe et al. |
| 8,244,327 B2 | 8/2012 | Fichtinger et al. |
| 2003/0004439 A1 | 1/2003 | Pant et al. |
| 2003/0018266 A1 | 1/2003 | Makin et al. |
| 2003/0069502 A1 | 4/2003 | Makin et al. |
| 2003/0092988 A1 | 5/2003 | Makin |
| 2003/0187347 A1 * | 10/2003 | Nevo ............ A61B 5/06 600/424 |
| 2005/0054913 A1 * | 3/2005 | Duerk ............ G01R 33/287 600/423 |
| 2006/0122514 A1 * | 6/2006 | Byrd ............ A61B 5/064 600/466 |
| 2006/0206105 A1 | 9/2006 | Chopra et al. |
| 2006/0241368 A1 | 10/2006 | Fitchtinger et al. |
| 2006/0241442 A1 | 10/2006 | Barthe et al. |
| 2007/0021648 A1 | 1/2007 | Lenker et al. |
| 2007/0106157 A1 | 5/2007 | Kaczkowski et al. |
| 2007/0239062 A1 | 10/2007 | Chopra et al. |
| 2008/0242970 A1 | 10/2008 | Minagawa et al. |
| 2009/0143775 A1 | 6/2009 | Rizoiu et al. |
| 2009/0171185 A1 | 7/2009 | Chou et al. |
| 2010/0033188 A1 | 2/2010 | Rieth |
| 2011/0034833 A1 | 2/2011 | Chopra et al. |
| 2011/0092824 A1 * | 4/2011 | Veen ............ A61B 5/14551 600/477 |
| 2011/0144524 A1 | 6/2011 | Fish et al. |
| 2011/0282156 A1 | 11/2011 | Lenker et al. |
| 2015/0338477 A1 | 11/2015 | Schmidt et al. |

OTHER PUBLICATIONS

Chopra et al., IEEE Transactions on Ultrasonics, Ferroelectrics, and Frequency Control, 50(7):881-889, 2003.
Diederich et al., Med. Phys., 31(2):405-413, 2004.
Kowalski et al., Phys. Med. Biol., 48:633-651, 2003.
Lafon et al., Ultrasonics, 36:683-687, 1998.
Lafon et al., Ultrasound Med. Biol., 30(1):113-122, 2004.
McNichols et al., Lasers Surg. Med., 34:48-55, 2004.
Ross et al., Phys. Med. Biol., 49:189-204, 2004.
Smith et al., Int. J. Hyperthermia, 17(3): 271-282, 2001.
Vanne et al., Phys. Med. Biol., 48: 31-43, 2003.
H. L. Liu et al., "Pilot point temperature regulation for thermal lesion control during ultrasound thermal therapy", Med. Biol. Eng. Comput., 2004, p. 178-188, vol. 42.
M. Burtnyk et al., "Quantitative analysis of 3-D conformal MRI-guided transurethral ultrasound therapy of the prostate: Theoretical simulations", International Journal of Hyperthermia, Mar. 2009, p. 116-131, vol. 25, No. 2.
European Patent Office, "Extended European Search Report—Application No. 12835517.9", dated Oct. 27, 2015, EPO.
D. Arora, M. Skliar & R. B. Roemar, "Model-Predictive Control of Hyperthermia Treatments", IEEE Transactions on Biomedical Engineering, Jul. 2002, p. 629-39, vol. 49, No. 7.

* cited by examiner

ULTRASONIC THERAPY APPLICATOR AND METHOD OF DETERMINING POSITION OF ULTRASONIC TRANSDUCERS

RELATED APPLICATIONS

This application is a continuation-in-part of U.S. patent application Ser. No. 12/932,920, titled "Ultrasonic Therapy Applicator," filed on Mar. 9, 2011, which claims priority to U.S. Provisional Application No. 61/311,853, titled "Ultrasonic Therapy Applicator," filed on Mar. 9, 2010, which are hereby incorporated by reference.

TECHNICAL FIELD

The present application relates to ultrasound therapy systems, and particularly to the construction and operation of an array of ultrasound sources for use in such systems.

BACKGROUND

Ultrasonic transducers have been employed in ultrasound therapy systems to achieve therapeutic heating of diseased and other tissues. Arrays of ultrasound transducers operating to form a beam of ultrasonic energy cause a conversion of sound to thermal energy in the affected tissue areas or treatment volumes, and a subsequent beneficial rise in the temperature in the treatment volumes. With proper monitoring of the heating effect, ultrasound therapy systems can be used to treat harmful cells and to controllably destroy cancerous tumors. The ultrasound transducers can be controlled by driving signals so as to provide a determined driving voltage, current, amplitude, waveform, or frequency of ultrasound energy.

As known to those skilled in the art, ultrasonic transducers are constructed and operated to take electrical power and produce ultrasound energy waves from a surface of a transducer element in a process generally referred to as transduction. The nature and extent of the transduction depends on the material used to construct the transducers, transducer geometry, and the electrical input to the transducers. A common material used in construction of ultrasound transducers is piezo-electric transducer crystal material (lead zirconate titanate (i.e., PZT)) which comes in several forms.

Various designs for ultrasonic array systems have been used in the present field of art. The present disclosure will not provide a detailed exposition of the prior arrays. Ultrasound array design can be challenging, and improvements to such designs would improve the effectiveness, safety and cost to manufacture of such arrays.

SUMMARY

Embodiments hereof are directed to systems and methods for providing an image-guided thermal therapy system including an ultrasonic array of transducers. In some respects, the present disclosure provides improved ultrasonic array designs to achieve better thermal therapy in such situations as trans-urethral prostate cancer therapy.

An aspect of the invention is directed to an apparatus for thermal therapy in a subject. The apparatus comprises an elongated cylindrical body having a first end thereof sized and configured for insertion into a male urethra; an array of ultrasonic sources disposed within said elongated cylindrical body and substantially arranged along an axis of said elongated cylindrical portion proximal to said first end of the elongated cylindrical portion, the ultrasonic sources being electrically driven to provide thermal therapy to said subject; a first fiducial marker disposed between said array of ultrasonic sources and said first end of said elongated cylindrical body; a second fiducial marker disposed between said array of ultrasonic sources and a second end of said elongated cylindrical body; a transition body portion directly connected to said second end of said elongated cylindrical body, said transition body portion including a flared portion that limits a depth of said insertion into said male urethra and a flanged portion, said flanged portion disposed between said second end and said flared portion; an elongated printed circuit board disposed in said elongated cylindrical body and extending from said first end of said elongated cylindrical body to said transition body portion such that a portion of said elongated circuit board is disposed outside said depth of said insertion, said circuit board including a plurality of printed circuit lines respectively coupled to a plurality of said ultrasonic sources of said array, said circuit lines providing power and control signals to said respective plurality of ultrasonic sources and driving said sources to deliver acoustic emissions of respective frequency and power depending on the respective power and control signals, said plurality of circuit lines on said circuit board being electrically and mechanically coupled to said plurality of ultrasonic sources of said array by way of respective conducting epoxy points or pads of finite thickness so as to cause a gas-filled separation between back sides of said ultrasonic sources and said circuit board therefore so as to cause an outward radiation of ultrasonic energy from an outward face of said ultrasonic sources, wherein said epoxy points or pads are disposed between said ultrasonic sources and said circuit board, said gas-filled separation having a width determined by said thickness of said epoxy points or pads and a height determined by a distance between adjacent epoxy points or pads; a rotational mechanical coupling directly connected to said flanged portion that supports and secures said elongated cylindrical portion, said rotational mechanical coupling further designed and arranged to permit mechanical rotation of said elongated cylindrical portion about said axis thereof and including a geared wheel configured to mechanically engage a rotational driver to convert a rotational movement of said driver to a corresponding rotational movement of said geared element; and at least one fluid conduit running through said rotational mechanical coupling permitting a fluid to circulate into and then out of said apparatus by flowing from said second end towards said first end of the elongated cylindrical portion and back again.

In one or more embodiments, said first fiducial marker comprises a fiducial cavity. In one or more embodiments, said fiducial cavity comprises an internal cavity disposed in said elongated cylindrical body. In one or more embodiments, said second fiducial marker includes an acoustic window defined on said elongated cylindrical body.

In one or more embodiments, the apparatus further comprises a complementary attachment mechanism comprising: a female body member having apertures defined therein, said female body member disposed on a tube in the elongated cylindrical body, the elongated printed circuit board disposed partially in said tube; and a male body member having tabs that engage the apertures in the female body member, said male body member disposed on the transition body portion. In one or more embodiments, the female body member is tubular and said male body member is cylindrical. In one or more embodiments, each aperture includes a first portion that extends axially with said female body member and a second portion that extends circumferentially with respect to said female body member. In one or more embodiments, the second portion of a first aperture extends circumferentially in a first direction and said second portion of a second aperture extends circumferentially in a second direction, said second direction opposite to said first direction.

In one or more embodiments, the apparatus further comprises a tube in the elongated cylindrical body, the elongated printed circuit board disposed partially in said tube, said comprising brass. In one or more embodiments, the tube is segmented and adjacent segments are separated by a gap, whereby the gap disrupts a current flow in said elongated cylindrical body. In one or more embodiments, the apparatus further comprises a rigid, non-conductive material disposed in each gap.

In one or more embodiments, the apparatus further comprises an inclinometer chip disposed on said elongated printed circuit board proximal to said plurality of said ultrasonic sources. In one or more embodiments, the apparatus further comprises tracking coils integrated in said elongated printed circuit board. In one or more embodiments, a first tracking coil is disposed on a distal side of said ultrasonic sources and a second tracking coil is disposed on a proximal side of said ultrasonic sources.

Another aspect of the invention is directed to a method for determining a position of ultrasound transducers disposed in a thermal therapy applicator. The method comprises: with a controller in communication with said thermal therapy applicator, rotating said thermal therapy applicator, disposed in a subject, such that an acoustic window in said thermal therapy applicator is oriented in a predetermined direction; acquiring a three-dimensional image of said subject, including said rotated thermal therapy applicator, with a magnetic resonance imaging apparatus; with said controller, identifying at least two fiducial markers in a first plane; with said controller, identifying at least one fiducial marker in a second plane, the second plane orthogonal to the first plane, wherein said at least one fiducial marker includes a line corresponding to an acoustic window defined in a tube disposed in a cylindrical shaft of said thermal therapy applicator; and with said controller, using said at least two fiducial markers and said at least one fiducial marker to determine said position of said ultrasound transducers, said ultrasound transducers coupled to a printed circuit board disposed in said tube.

In one or more embodiments, the location of said ultrasound transducers is determined based at least in part on a predetermined relative orientation of said tube with respect to a handle of said thermal therapy applicator. In one or more embodiments, the method further comprises securing said printed circuit board to a handle, thereby fixing the predetermined relative orientation of said ultrasound transducers to said handle.

In one or more embodiments, the method further comprises, using said controller, directing a thermal therapy to said subject based on said position of said ultrasound transducers. In one or more embodiments, the first plane corresponds to a Sagittal plane and said second plane corresponds to a Coronal plane. In one or more embodiments, the predetermined direction corresponds to a posterior of said subject.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

As discussed above, improved ultrasound thermal therapy applicators can improve treatment of diseases such as tumors, and for example as used in trans-urethral treatment of prostate cancers in male patients.

Figure 1:
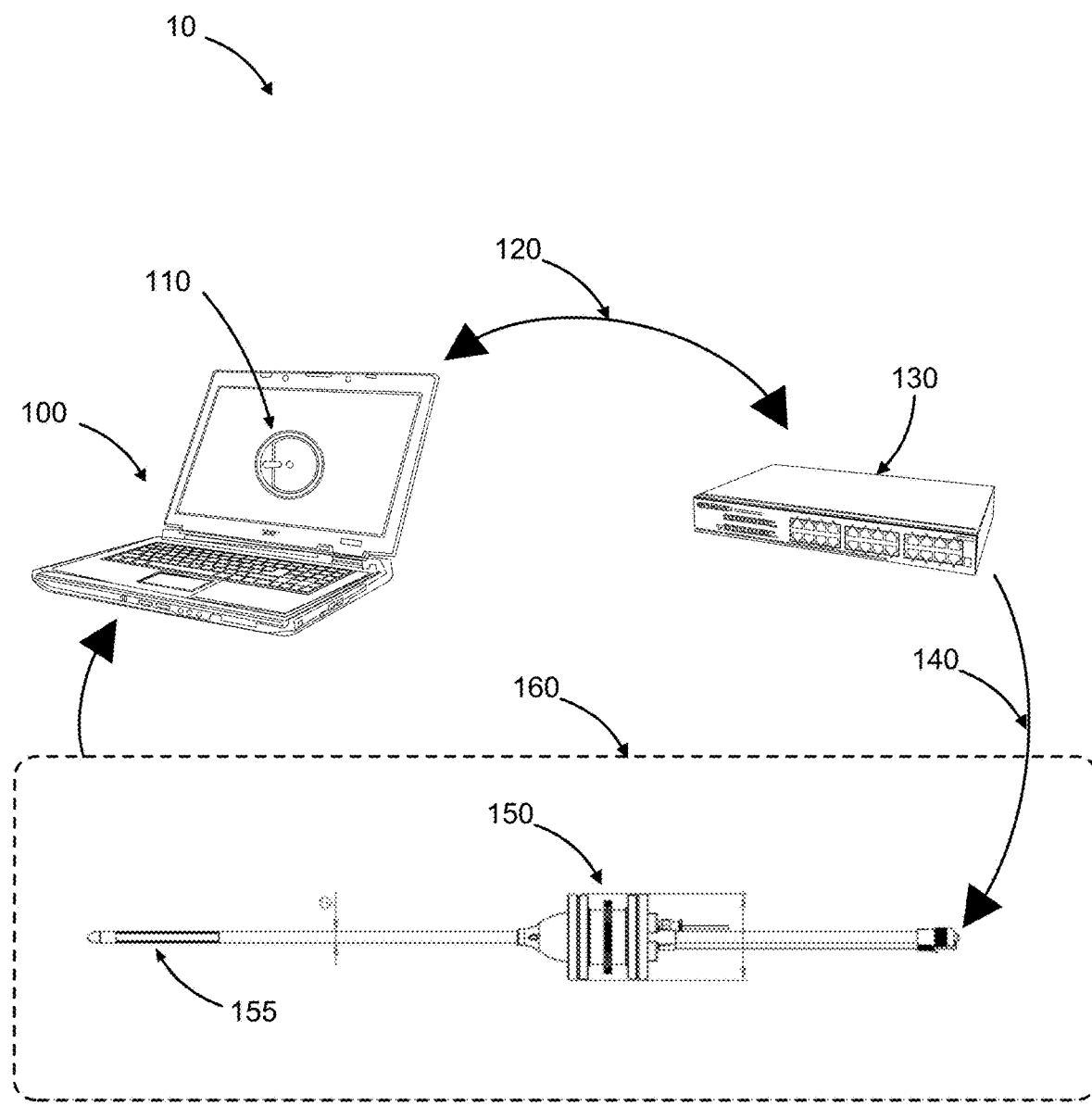
FIG. 1 illustrates an exemplary system for providing image-guided ultrasound therapy to a patient.

FIG. 1 illustrates an exemplary system 10 for providing image-guided ultrasound therapy to a patient. The simplified illustration shows a master computer 100, such as a portable PC, workstation, or other processing device having a processor, memory, and coupled to some input/output apparatus. Master computer 100 may include a display and may support a user interface 110 to facilitate control of and observation of the thermal therapy treatment process.

Master computer 100 is adapted for coupling to other systems and components through a computer interface connector 120. Connection 120 carries data and information to and from master computer 100 and may comprise standard or special-purpose electrical wiring connection cables, such as serial connection cables or the like. Also, connection 120 may be achieved wirelessly as known to those skilled in the art of wireless communication, and may further be achieved by way of multiple connections, over a network, or by another suitable method.

In some embodiments, master computer 100 is coupled through connection 120 to a power control unit 130. Power control unit 130 may be implemented as a stand-alone hardware apparatus but may be implemented as a part of master computer 100, e.g., by being built onto a special card in a computer or server system that accommodates such hardware components.

Power control unit 130 may specifically include at least a processor adapted for processing machine or program instructions, which may be provided to the processor from another component of system 10 and may be stored on a memory device in power control unit 130. Circuitry including analog and/or digital circuitry may be operated within power control unit 130 so as to determine an output power to one or more ultrasound therapy transducer elements in an ultrasound therapy apparatus 150.

In some embodiments, power control unit 130 may deliver controlled electrical driving signals to a plurality of ultrasound transducer elements (e.g., PZT array elements) in ultrasound therapy apparatus 150. The driving signals may be controlled to deliver a programmed amount of power to each element or to groups of elements of therapy apparatus 150. The driving signals may also be controlled so as to provide a determined driving voltage, current, amplitude, waveform, or frequency to said ultrasonic transducers of therapy apparatus 150. Such electrical driving signals are carried from power control unit 130 to the ultrasound therapy apparatus 150 over suitable wires, cables, or buses 140. Appropriate plug interfaces or connectors may be included so as to mate the various ends of the connectors or buses to and from their associated components.

In operation, ultrasound therapy apparatus 150 includes a portion 155 that is inserted into a portion of a patient's body to deliver a suitable dose of ultrasound energy to tissue in a diseased region of the patient's body.

The patient and the ultrasound therapy apparatus 150 are generally disposed in an imaging volume 160 such as a magnetic resonance imaging (MRI) apparatus, which can provide real-time images of the relevant parts of the patient, e.g., the treatment volume to master computer 100 or display and user interface 110. In some embodiments, real-time monitoring of the thermal therapy is performed so that a clinical operator can monitor the progress of the therapy within the treatment volume or diseased tissue. Manual or automated changes can be made to the power signals from power control unit 130 based on input from the results and progress of the treatment.

The feedback and coupling of the treatment system components to the control components in system 10 can be used to ensure that an optimum radio frequency (RF) power signal is provided to each element of an ultrasound array 155 used in treatment of diseased tissues. Some examples include treatment of prostate cancer tumors in male patients using MRI guided ultrasound therapy applications.

RF power control unit 130 may include separate circuit cards having individual processors, amplifiers, filters and other components to achieve the desired driving power output to the elements of ultrasound array 155 of ultrasound treatment apparatus 150. Alternatively, a single processor may be employed to control the behavior of the various power channels to each array element.

Figure 2:
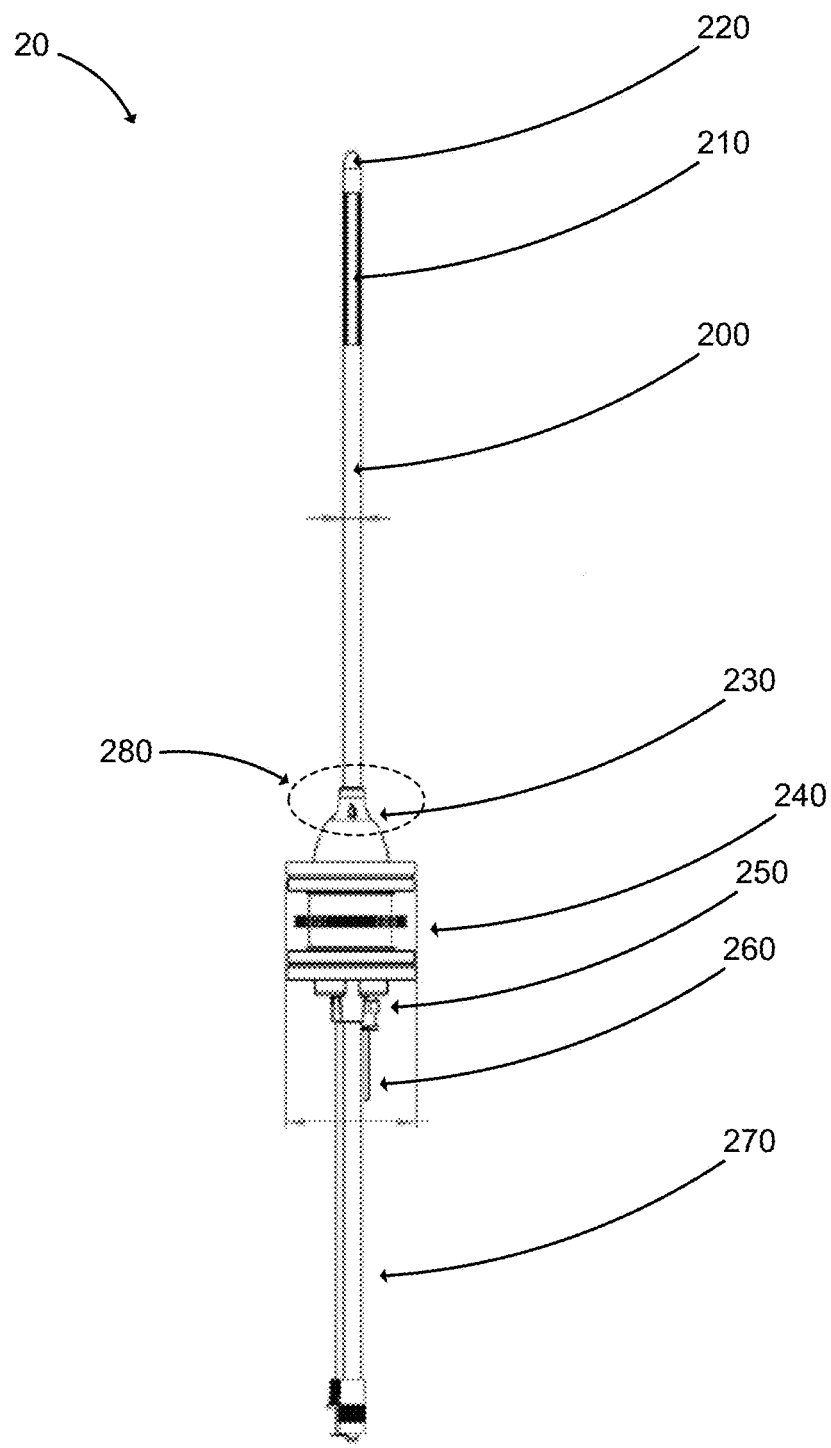
FIG. 2 illustrates an exemplary design of an elongated ultrasound thermal therapy applicator.

FIG. 2 illustrates an exemplary ultrasound therapy applicator design. Applicator 20 includes an elongated shaft portion 200, which can be inserted into a body cavity proximal to a diseased tissue region of a patient. In some instances, elongated shaft portion 200 (or a portion thereof) may be inserted into the urethra of a male patient to treat diseased tissue such as cancerous tissue of the male prostate. The insertion of applicator 20 into the patient is done by pressing the applicator 20 into an appropriate channel, optionally using image guidance such as MRI or X-ray guidance to monitor the movement of applicator 20 within the patient.

The applicator 20, or typically the elongated shaft portion 200, are inserted into the patient until the transducer array 210 reaches an area proximal to the diseased tissue volume or target volume for the thermal therapy. In this way, when power is provided to the transducer array 210 it will cause a controlled heating of the diseased tissue volume to treat the disease condition or affect some other desired outcome. Tip 220, as will be discussed below, may be constructed of blunt smooth material such as a polymer or metal material to assist in easy reduced friction insertion and movement of applicator 20 into the patient. In some embodiments, this design minimizes frictional stress on the interior walls of the patient's urethra.

A transition portion 230 of applicator 20 is flared or bulbous in shape and provides a safety zone that prevents unwanted portions of apparatus 20 from entering into the patient's body.

Flanged portions of transition portion 230 allow for easier manipulation of applicator 20 and mechanical control of the same as will be described below in further detail. The portion 230 can act as a handle for holding the applicator and may be constructed of an optically transparent material such as clear plastic. This can allow viewing of the interior of the apparatus in some situations to determine if any gas (air) bubbles have been trapped in the fluid circuit portion of the apparatus. The gas can then be vacated to minimize or avoid interference in the transmission of ultrasound energy from the transducer system or interference with the cooling fluid flow within the body of the system. The flanges can also provide a mechanical means for holding applicator 20 in place within a bearing system or rotation and translation driver used to move and rotate applicator 20 during operation.

A geared element 240 provides a mechanically-compatible actuation means for rotating applicator 20 within the patient's body so that array 210 is properly and controllably rotated about the long axis of shaft 200 to treat a volume of tissue up to a complete 360-degree rotation volume surrounding the axis of shaft 200 if desired. In some embodiments, a motor is adapted for driving the gear 240 of applicator 20 to provide such rotation of the applicator within the patient about the long axis of the applicator. As discussed below, a complementary attachment can be included to secure a tube in shaft 200 to handle (e.g., to transition portion 230). The complementary attachment mechanism can include a hole or a notch and a corresponding protrusion, which fixes the relative position of the tube (and ultrasound transducers) to the rotating handle.

Mechanical interfaces 250 allow coupling of fluid intake and outtake connections to applicator 20 so that temperature control fluid can be passed into and out of the applicator 20. For example, in situations where cooling of the applicator itself or surrounding tissue in needed, the fluid can be applied to these interfaces optionally using standard fluid hook-up connectors and tubing 270. Also, electrical wiring 260 or micro-buses can be passed through interfaces 250 to provide electrical driving power to the elements of transducer array 210 and to receive sensor signals or other signals and data from the components of applicator 20. Again, standard electrical connectors may be used to interface outside power and control systems with the internal electrical elements of applicator 20.

In operation, applicator 20 may be placed with tip 220 proximal to an aperture in the patient's body and with the long axis of shaft 200 substantially aligned with a cavity or channel (e.g., the urethra) of the patient for insertion therein. The applicator 20 is then automatically or manually or by a combination of the two inserted into the patient's body, beginning with tip 220 end of shaft 200. When the applicator 20 is sufficiently inserted into the patient's body (e.g., using image guided translation motor stages) the translation of applicator 20 is secured. Then, a computer-controlled thermal therapy procedure is undertaken, with applicator 20 being rotated about its long axis within the patient's body so that transducer array 210 provides a therapeutic energy field such as an ultrasonic field of known strength and nature to treat the diseased tissue proximal to array 210. When the thermal therapy is completed, power to ultrasound array 210 is secured and applicator 20 is retracted from the patient substantially along the long axis of the applicator, in substantially the reverse direction as it was inserted.

Figure 3:
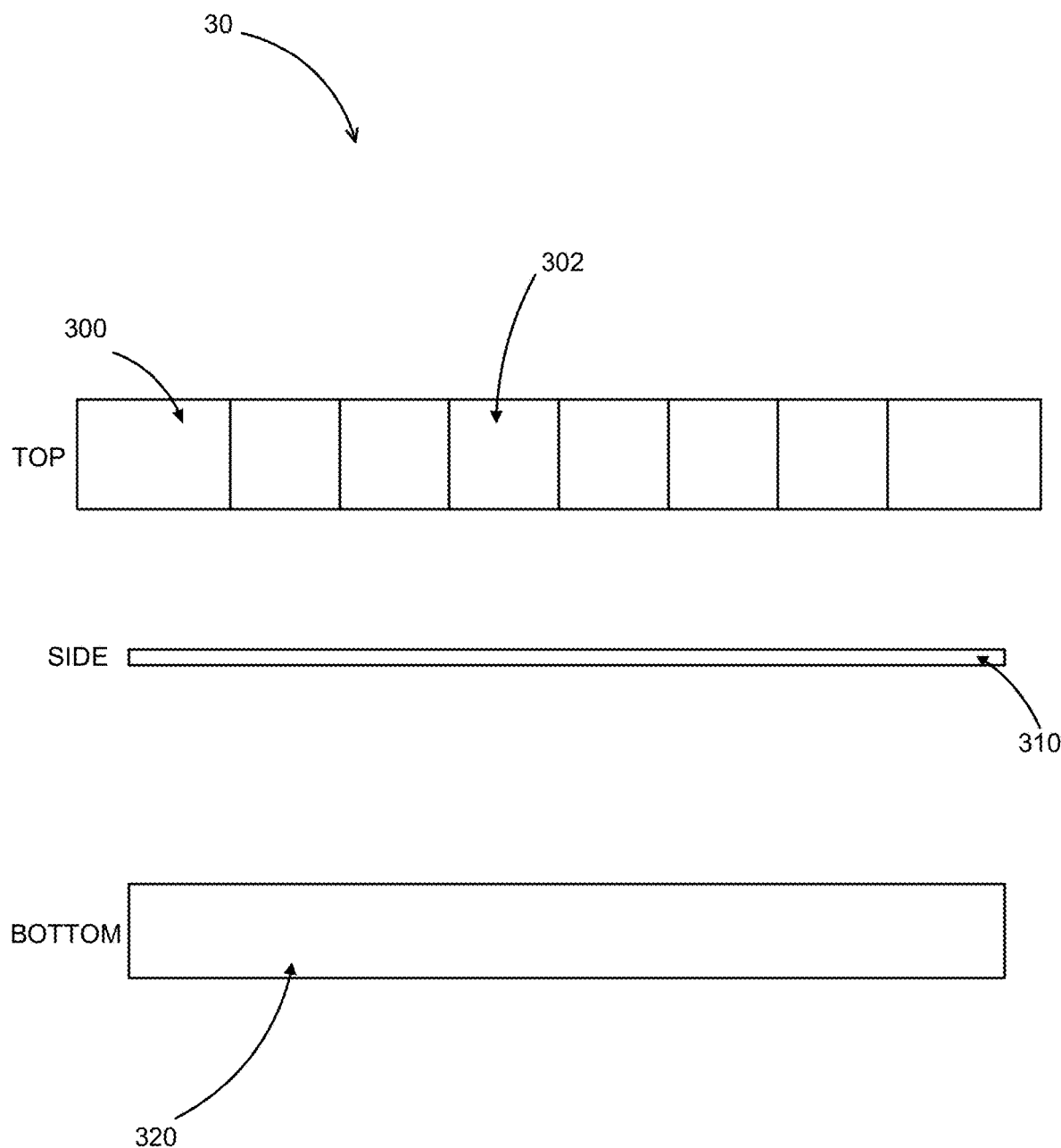
FIG. 3 illustrates an exemplary ultrasonic array for use in an ultrasound therapy system.

FIG. 3 illustrates an exemplary design for the transducer array (such as array 210 of FIG. 2). An ultrasonic array 30 is shown as it appears from the "top" face thereof at view 300. Note that in the present illustration the "top" face is the face of the array normally facing into the center of the applicator shaft and away from the patient's body. The same array is shown from the side in view 310. The opposing or "bottom" view of the array is shown in view 320, and is the face of the array which is outwardly directed at the patient's treatment volume and away from the applicator. It is seen that in this exemplary embodiment the ultrasonic array is constructed from a substantially flat or relatively planar material. This may be a PZT-based material as is generally known to those skilled in the art. In some embodiments, the material may comprise K320 from Piezo Technologies of Indianapolis, Ind. USA. Alternately, it may be made of PZ52 or similar material from Ferroperm Piezoceramics of Kvistgaard, Denmark. The array and its elements may be designed and arranged to have a pre-determined optimal resonance frequency, for example 4 MHz, or other central frequency for best penetration and power delivery to the diseased volume of tissue, in some embodiments, along with the third harmonic at approximately 13 MHz as well.

According to the present embodiment, the front face of transducer array 30 is cut into a plurality of individual array elements, e.g., 302. The individual elements 302 may or may not all be of the same shape and size. The dimensions given in the figure are merely illustrative. In certain embodiments, the elements 302 are substantially rectangular or square in shape and provide an ultrasonic energy field proximal to the face of elements 302 as dictated by the design, material and driving signals for the elements 302. The elements 302 of array 30 may be driven in a programmed way as discussed in other applications by the present inventors and assignee to create an overall ultrasonic therapeutic energy field within a controlled volume of tissue in a patient. The array 30 mounted to the rest of the therapy applicator may be rotated about the long axis of array 30 so as to provide treatment to a volume around array 30 as needed.

Both the front face 300 and the back face 320 of array 30 are silvered to permit delivery of driving power signals to and grounding of the elements of array 30. The ends and edges (shown in 310) of array 30 may be left unsilvered. In this way, some or all of elements 302 may be powered by an appropriate power source.

In some embodiments, one or both elements at the ends of array 30 may be "dummy" elements that are not substantially driven or used for the actual thermal therapy in operation of the device.

Figure 4:
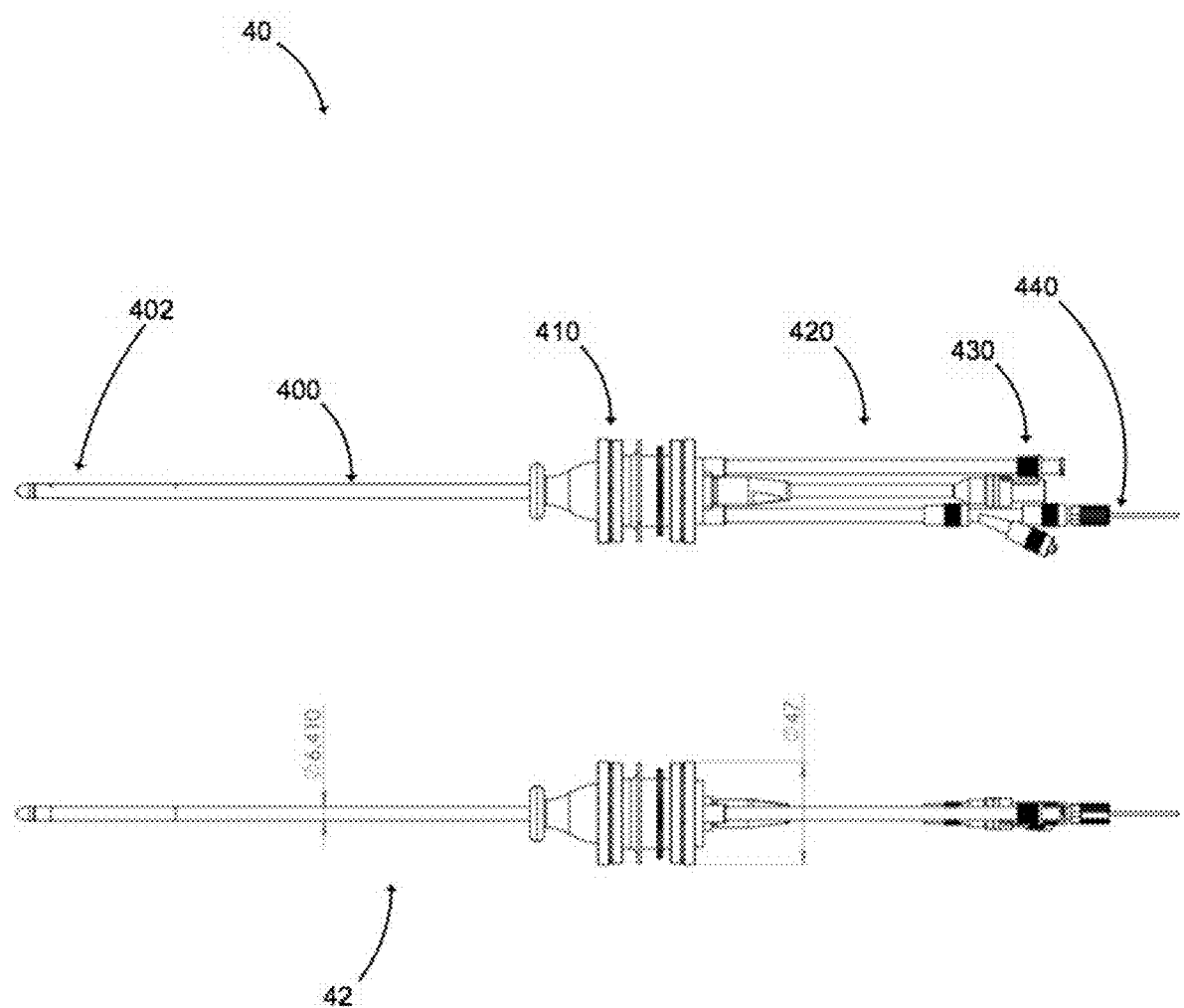
FIG. 4 illustrates two views of an elongated ultrasonic thermal therapy applicator according to exemplary embodiments hereof.

FIG. 4 illustrates two views 40 and 42 of an illustrative ultrasound therapy applicator device, showing the exemplary arrangement of the connectors and transitional mechanical elements thereof with respect to the elongated shaft and transducer array portions as described above. An elongated portion 400 is designed for insertion into a male urethra, optionally by applying an acoustically-compatible lubricant or disinfecting liquid or gel to an exterior of elongated portion 400. Ultrasound elements are arranged within and running along a portion near the tip 402 of elongated applicator 400. This is the part of the apparatus which is inserted into the patient's body until it is substantially situated within a volume of diseased tissue (e.g., the prostate) and from which the ultrasonic thermal energy is emitted into the diseased tissue.

The elongated portion is supported by and secured to one or more flanged elements of the applicator body, which in a preferred embodiment act as bearings 410 or gear elements to assist in rotating the applicator about its long axis once the applicator's tip is at the desired depth within the patient. In some aspects, a motorized driver as described elsewhere by the present applicant is used to mechanically rotate and/or translate the apparatus.

For example, in a preferred embodiment, the applicator 40, 42 is inserted into a patient who is lying on and secured to a bed, table, or platform. Once inserted to the proper position in the patient so that the ultrasonic array in portion 402 of the applicator is proximal to the diseased tissue, a rotational stepper motor or other piezo-electric driver is used to mechanically turn the apparatus and hence the ultrasonic array of the apparatus about its axis so as to sonicate the diseased tissue (prostate) to the desired degree using computer-controlled power, frequency or other electrical driving signals delivered to the elements of the array at 402.

As discussed elsewhere in this disclosure, electrical and mechanical (e.g., fluid) connections are made from portions of the applicator outside the patient's body to portions of the applicator inserted into the patient's body. Preferably, such mechanical and electrical connections employ physically compact components to reduce the discomfort felt by the patient and to reduce the chances of strain on the patient's healthy organs (e.g., urethra). Accordingly, in an embodiment, fluid conduits 420 into and out of the patient are provided with appropriate transitional or coupling ends and deliver electrical or fluid content to and from the elongated portion 400 and proximal to tip end 402 of the apparatus. Further coupling using fluid couplings 430 and electrical couplings 440 are provided, and these couplings are connected to corresponding parts of the fluid circuit pumping fluid into the applicator and out of the same and electrical circuits delivering power and control capability to the system, respectively.

Figure 5:
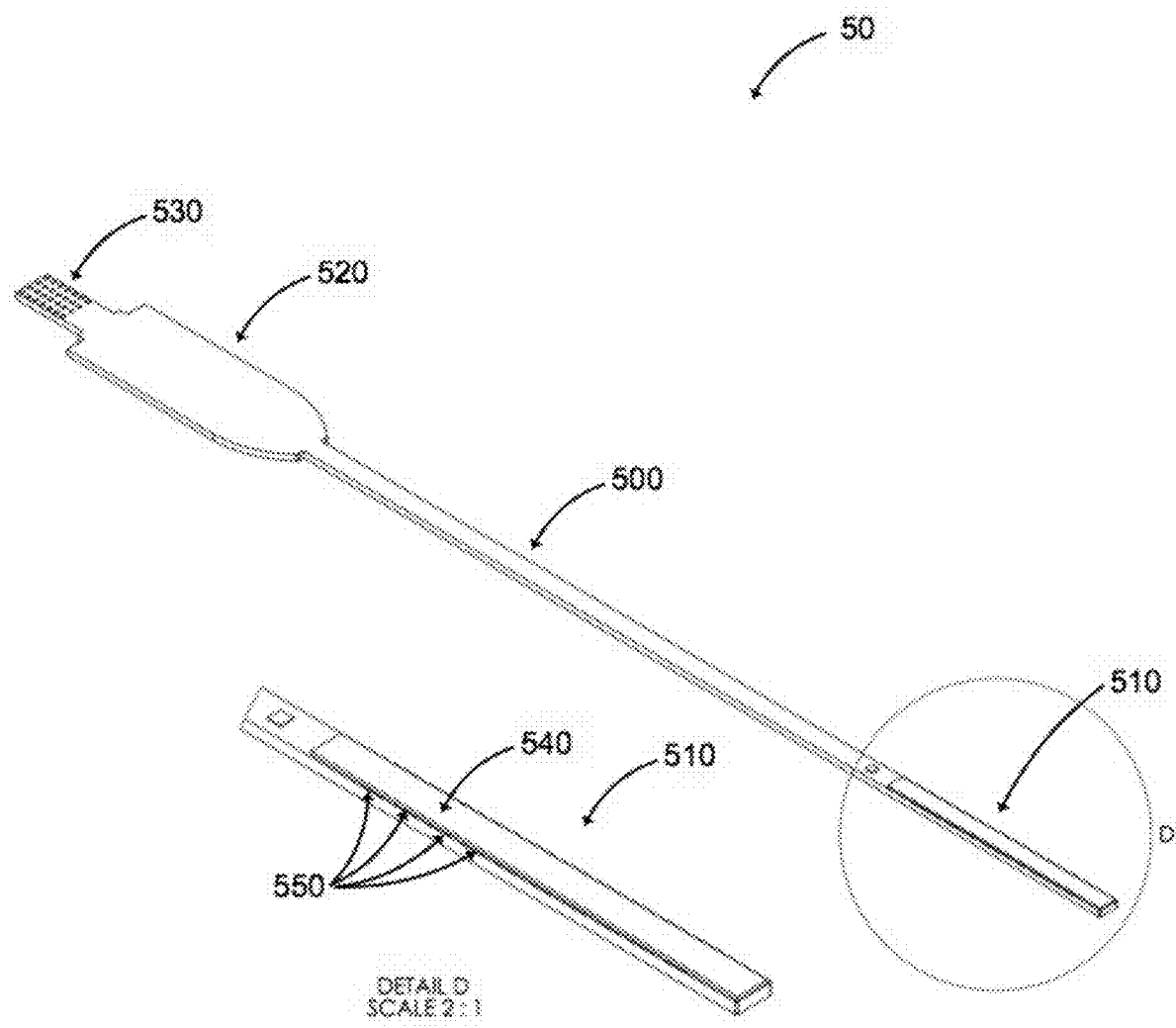
FIG. 5 illustrates an exemplary sequence for a method used in ultrasound thermal therapy.

FIG. 5 illustrates an exemplary internal view of the transducer support and assembly member 50, on which the ultrasonic array is supported and on which the circuitry for driving the elements of the array are mounted. In the present embodiment, an elongated substantially flattened and paddle-like shaped support member 50 has a long shaft section 500. Ultrasonic array 510 is disposed near a first end of said shaft section, and array 510 may be attached, fixed, mounted or adhered to said long section 500 by any means convenient or effective for a particular application and geometry.

A wider section 520 extends from a second end of elongated section 500 and is placed within a transitional portion of the therapy applicator and is generally not inserted into the patient's body. An electrical connection 530 is provided for connecting to the outside electrical power drive and control system.

In some embodiments, the support and assembly member 50 is made of or on or includes a printed circuit board (PCB) material. On the PCB, thin electrical connections are printed and run from electrical connector 530 up the shaft 500 to power the elements of transducer array 510.

A detail "D" of the array 510 end of the system is shown below in the same drawing. The common ground "bottom" face 540 of the transducer array is shown, as are several connection points 550 to the "top" face of the individual transducer elements on the opposing face of array 510. The individual wiring can be accomplished by placement of the array onto the PCB support member and soldering of connections between the PCB circuitry and the individual array elements so as to allow individual power and control of the same.

An inter-metallic bond or epoxy connection points can be used to couple the transducer elements to the PCB lines. The connection points form "pads" of a finite thickness. These pads cause the surface of the PCB and the surface of the transducers to be separated (e.g., by a thickness of about 0.003 inch). 3-oz copper pad connection points will provide approximately a 0.0034 inch air gap. As used herein, "about" or "approximately" means plus or minus 10% of the relevant value. The separation is air-filled or gas-filled so as to provide an "air backing" to the transducer array 510 so that the array directs its energy outwardly from the "bottom" face thereof, facing the patient, as opposed to radiating its energy through the top face or another direction. This spacing of the array and the support structure 500 is a design feature that eliminates the need for using a spacer to provide the air-backing in some embodiments. It is noted that the present exemplary dimensions and arrangements are given for the sake of illustration, and are not limiting, so that one of skill in the art would appreciate other forms and sizes and arrangements accomplishing substantially same or similar ends in similar ways.

Figure 6:
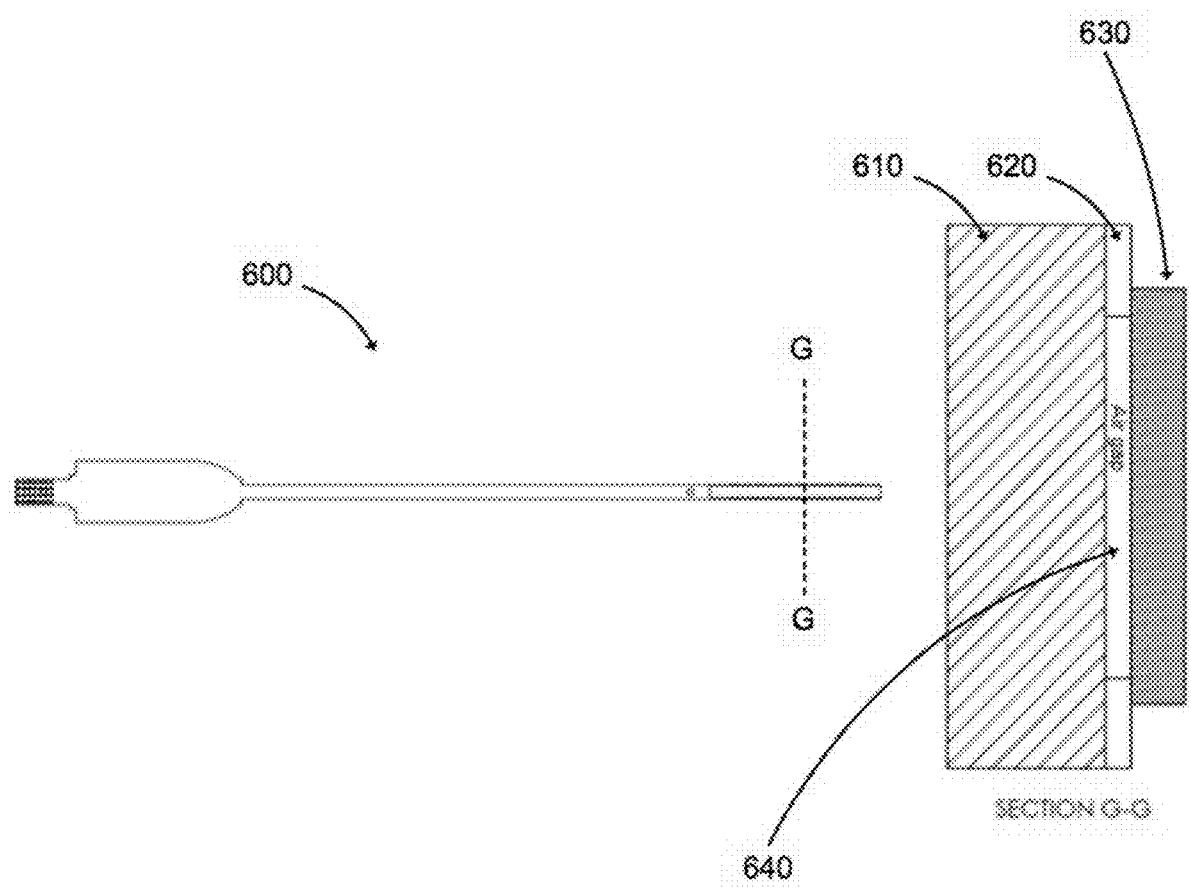
FIG. 6 illustrates a view of the circuit support member such as a PCB support member.

FIG. 6 illustrates a view of the circuit support member 600 such as the PCB support member described above. A section G-G is shown to the right to illustrate an exemplary arrangement of the silvered transducer element 630, which is coupled to the PCB material 610 by copper or other conducting pads 620. The pads 620 are of a thickness as described above to provide a suitable air gap 640 so that the transducers 630 are properly air-backed for transmitting ultrasonic energy from the bottom face of the elements 630 (to the right in FIG. 6) towards the diseased tissue of the patient.

Figure 7:
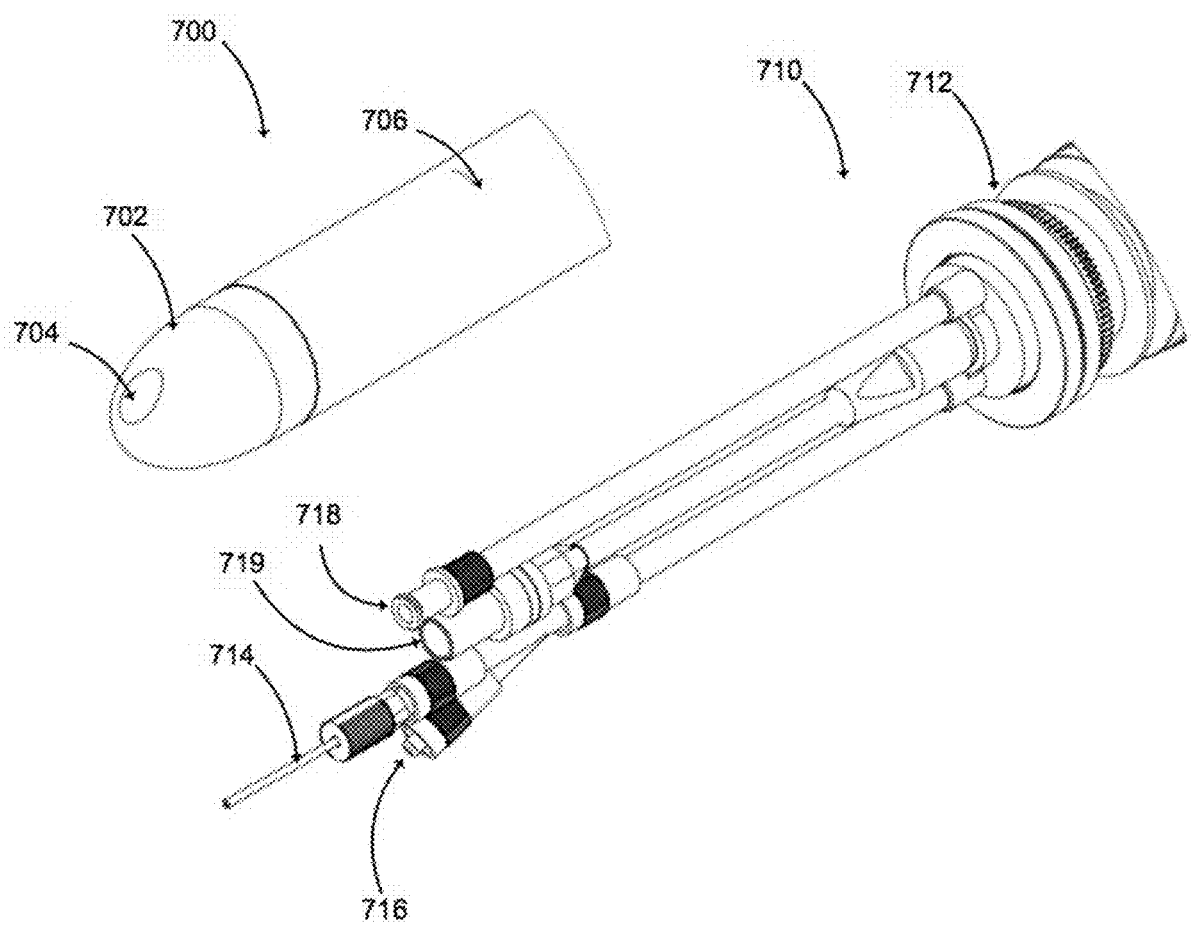
FIG. 7 illustrates exemplary designs of two ends of an ultrasound treatment applicator, one for insertion into a treatment volume of a patient's body and the other for coupling to mechanical and electrical components of the treatment system.

FIG. 7 illustrates exemplary designs of two ends of an ultrasound treatment applicator.

At one end 700 of the applicator, as discussed earlier, is a tip portion 702 coupled to the inserted end of the elongated shaft member 706 of the applicator. In some embodiments, a fiber optic or other temperature sensor is placed at or near the tip of the applicator for sensing the temperature in or near the tip of the applicator.

In some embodiments, a hole 704 or small orifice is disposed at or near the leading end of tip 702. The hole allows for drainage of fluid, e.g. urine that may collect in the patient near the tip end of the applicator. This can reduce the swelling or pressure in the patient near the treatment zone during a thermal therapy procedure. The fluid drained from the patient through hole 704 may be carried in a tube or channel down the length of the applicator apparatus to the opposite end of the applicator and outside the patient at exterior end 710 of the applicator.

End 710 of the thermal therapy applicator includes a catheter 714 in fluid communication with the hole 704 in tip 702. This catheter delivers fluid (e.g., urine) drained from the patient's body to a suitable retainer or receiving volume. The drained fluid can be monitored for blood, drugs, temperature, or other attributes. A valve or shut-off apparatus may be included in-line with catheter 714 to control the flow of fluid in or out of the catheter. In some embodiments fluid may be delivered in to the patient's body, including drug delivery to the patient near the tip 702 of the applicator.

Figure 8:
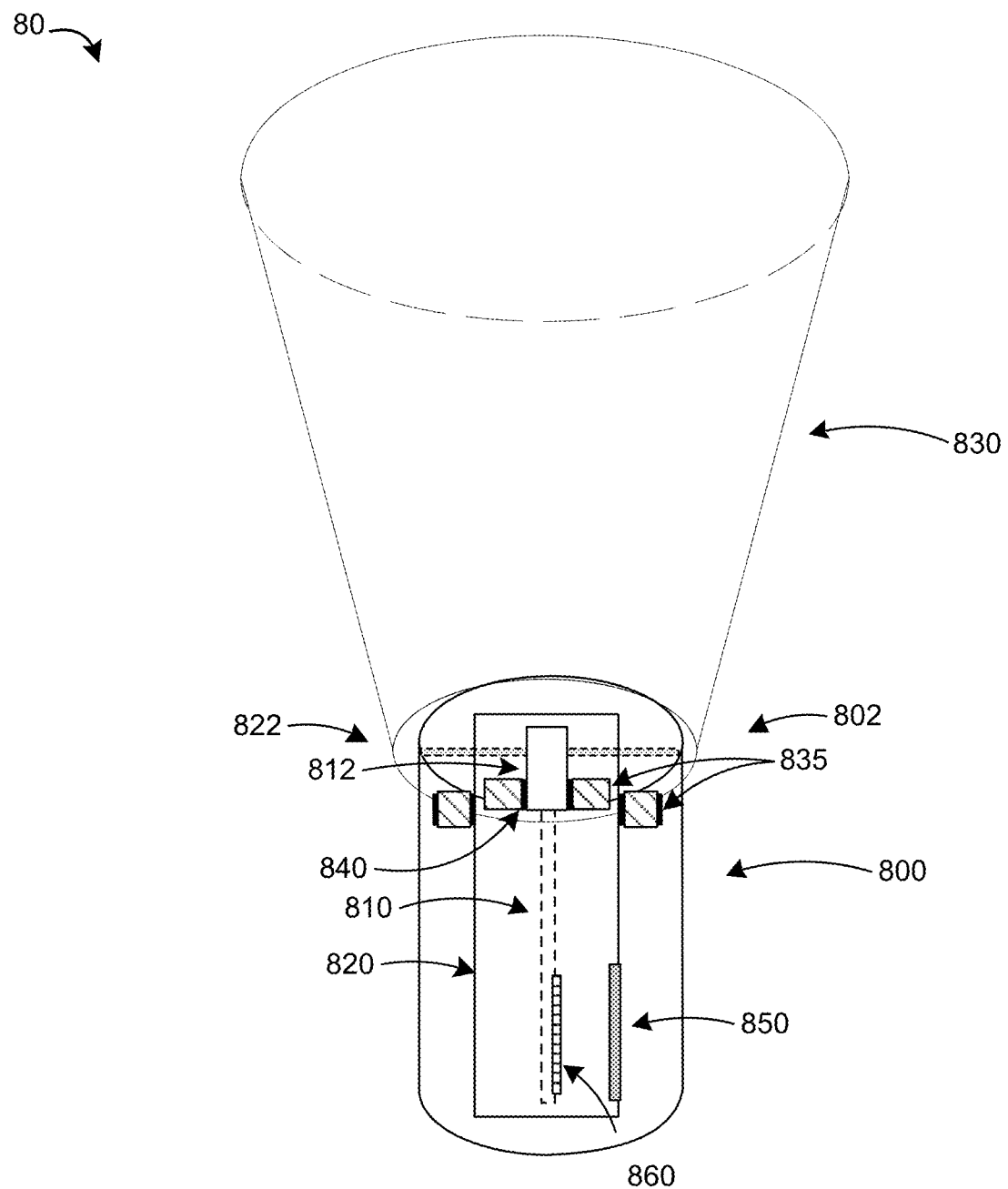
FIG. 8 illustrates a detailed view of the upper portion of elongated shaft portion and handle of a thermal therapy applicator according to one or more embodiments.

FIG. 8 illustrates a detailed view of the upper portion of elongated shaft portion 800 and handle 830 of thermal therapy applicator 80 according to one or more embodiments. In some embodiments, FIG. 8 is a detailed view of region 280 illustrated in FIG. 2. For example, handle 830 can correspond to transition portion 230. As illustrated in FIG. 8, a transducer support and assembly member 810 is disposed in a tube 820 in shaft portion 800. The tube 820 can be formed of or can comprise brass or other material that is substantially MRI compatible. The tube 820 can be covered with a thin layer of polyethylene terephthalate (PET). For example, the tube 820 can comprise brass and it can be covered with about a 0.002 inch thick layer or sheath of PET. PET is a generally biocompatible material that is substantially transparent to ultrasound, an insulator (e.g., to provide electrical safety insulation around tube 820), and can retain cooling water inside tube 820 (e.g., at acoustic window 850). The proximal end 812 of the transducer support and assembly member 810 is attached to one or more features 835 on the handle 830 by an adhesive 840. The adhesive 840 can be a glue, an epoxy, or other adhesive. Likewise, the proximal end 822 of tube 820 is attached to one or more features 835 on the handle 830 by adhesive 840. The adhesive 840 used to attach tube 820 to feature(s) 835 can be the same or different than the adhesive 840 used to attach transducer support and assembly member 810 to feature(s) 835. Attaching both the transducer support and assembly member 810 and tube 820 to features 835 on the handle 830 can set the relative positions and distances of transducer support and assembly member 810 and tube 820 with respect to one another and with respect to handle 830. Acoustic window 850 and transducers 860 are illustrated in FIG. 8 for context. Acoustic window 850 is an aperture or hole defined in the tube 820 to allow ultrasound to pass through, since tube 820 is not transparent to ultrasound.

In some embodiments, the features 835 on the handle 830 can engage with a complementary feature on tube 820, on the proximal end of 812 of the transducer support and assembly member 810, or on the proximal end 802 of shaft portion 800. (in general, "complementary features"). For example, the complementary feature can be a male or a female portion of an attachment mechanism while the features 835 on the handle 830 can have the complementary portion of the attachment mechanism. For example, if features 835 are male portions of an attachment mechanism, the complementary features are female portions of the attachment mechanism. Likewise, if features 835 are female portions of an attachment mechanism, the complementary features are male portions of the attachment mechanism.

Figure 9A:
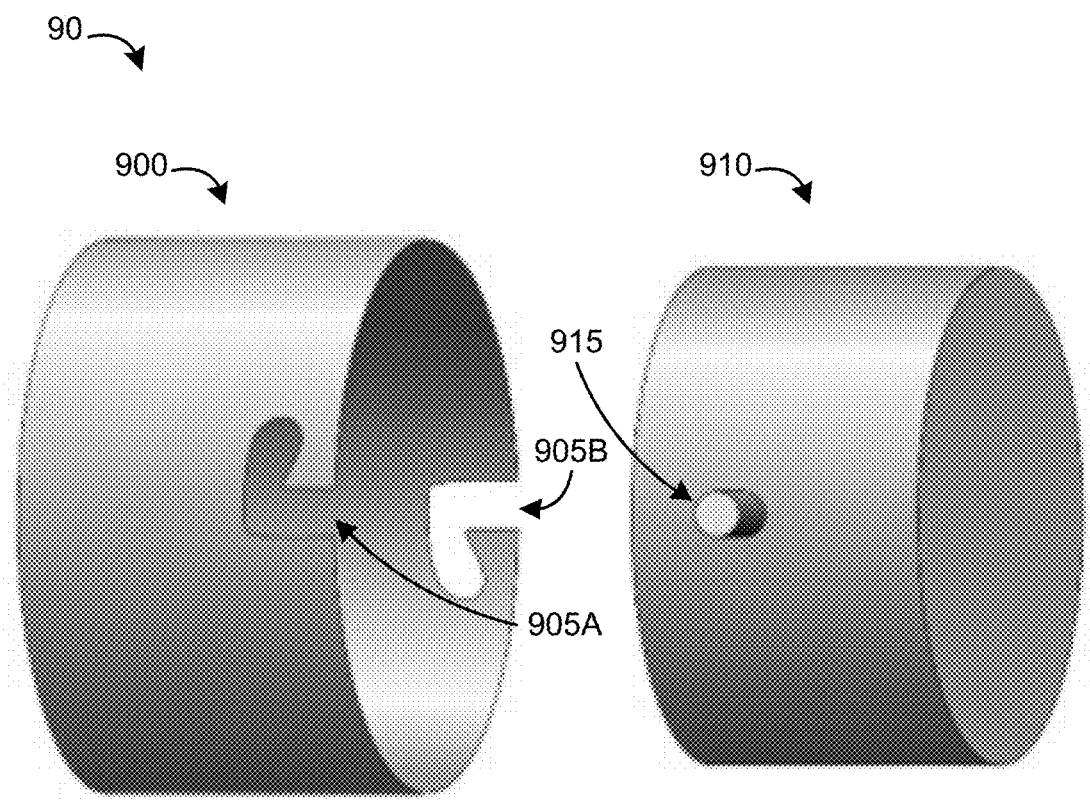
FIGS. 9A and 9B illustrate an example of a complementary attachment mechanism according to one or more embodiments.

An example of such a complementary attachment mechanism is illustrated in FIG. 9A, which illustrates a bayonet lock mechanism 90. The bayonet lock mechanism 90 includes a female body member 900 and a male body member 910. The female body member 900 is cylindrical and includes a pair of apertures or keyholes 905A, 905B (in general, apertures 905) that extend in opposite directions about the female body member 900. For example, as illustrated in FIG. 9A, aperture 905A includes a first portion that extends inwardly (e.g., axially with respect to tubular female body member 900) and a second portion that extends upwardly (e.g., circumferentially in a first direction with respect to tubular female body member 900), generally forming about a 90-degree angle between the first and second portions of aperture 905A. Aperture 905B includes a first portion that extends inwardly (e.g., axially with respect to tubular female body member 900) and a second portion that extends downwardly (e.g., circumferentially in a second direction with respect to tubular female body member 900), in FIG. 9A, generally forming about a 90-degree angle between the first and second portions of aperture 905B. Aperture 905A is disposed about 180 degrees from aperture 905B about the perimeter of female body member 900.

Male body member 910 includes a pair of projecting body portions or tabs 915 (only one tab 915 is illustrated in the perspective view of FIG. 9A). Each tab 915 is sized to fit securely in each aperture 905A, 905B. The tabs 915 are disposed about 180 degrees from each other such that they align with apertures 905A, 905B. In operation, the inward portions of apertures 905A, 905B first receive the tabs 915. Then, the female body member 900 rotates counterclockwise with respect to the male body member 910 such that the respective upward and downward portions of apertures 905A, 905B receive the tabs 915, at which point the bayonet lock mechanism 90 is engaged.

Figure 9B:
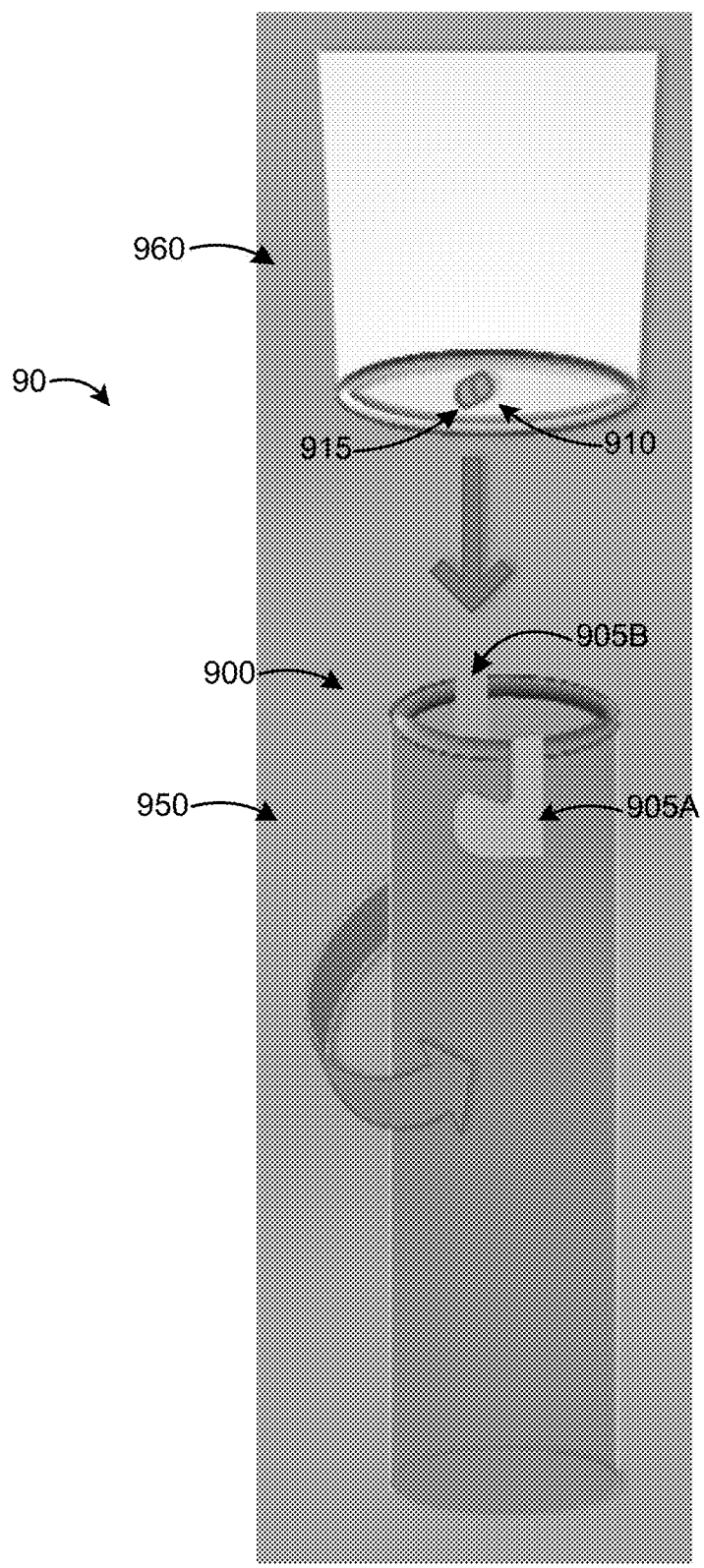

FIG. 9B illustrates the complementary attachment mechanism 90 disposed on a cylindrical body 950 and on handle member 960. The cylindrical body 950 can correspond to the tube (e.g., tube 820) or the shaft portion (e.g., shaft portion 800), as discussed above. As illustrated in FIG. 9B, the female body member 900 is disposed on the cylindrical body 950 and the male body member 910 is disposed on the handle member 960. However, the opposite configuration is also possible, as discussed above.

Figure 10:
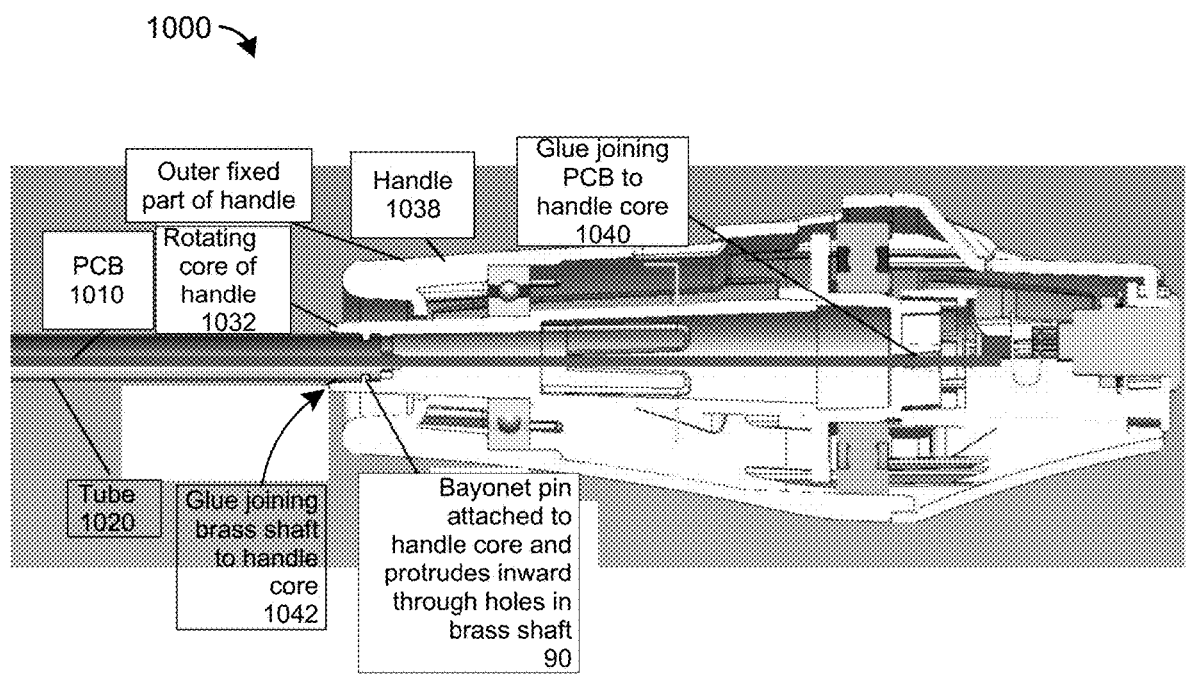
FIG. 10 is a cross-sectional view of the upper portion of elongated tube 1020 and handle 1030 of thermal therapy applicator 1000 according to one or more embodiments.

FIG. 10 is a cross-sectional view of the upper portion of elongated tube 1020 and handle 1030 of thermal therapy applicator 1000 according to one or more embodiments. This figure illustrates the bayonet lock mechanism 90 on thermal therapy applicator 1000. The bayonet lock mechanism 90 includes protrusions or tabs that extend inwardly from the rotating core 1032 of handle 1030. The protrusions or tabs engage corresponding holes (e.g., such as keyholes 905A, 905B) defined in the proximal end of tube 1020. An adhesive 1042, such as glue, is disposed between tube 1020 and handle 1030 at the proximal end of tube 1020 and distal end of handle 1030. The adhesive 1042 secures the tube 1020 to handle 1030 while the bayonet lock mechanism 90 provides a secondary means of securing tube 1020 to handle 1030, for example if the adhesive 1042 fails.

A PCB 1010 extends through the interior cavity of tube 1020 and of handle 1030. The proximal end of PCB 1010 is secured to the rotating core 1032 of handle 1030 with an adhesive 1040, such as glue. The adhesive 1040 fixes the relative orientation of PCB 1010 (and the transducers connected thereto) with respect to the rotating core 1032.

Figure 11:
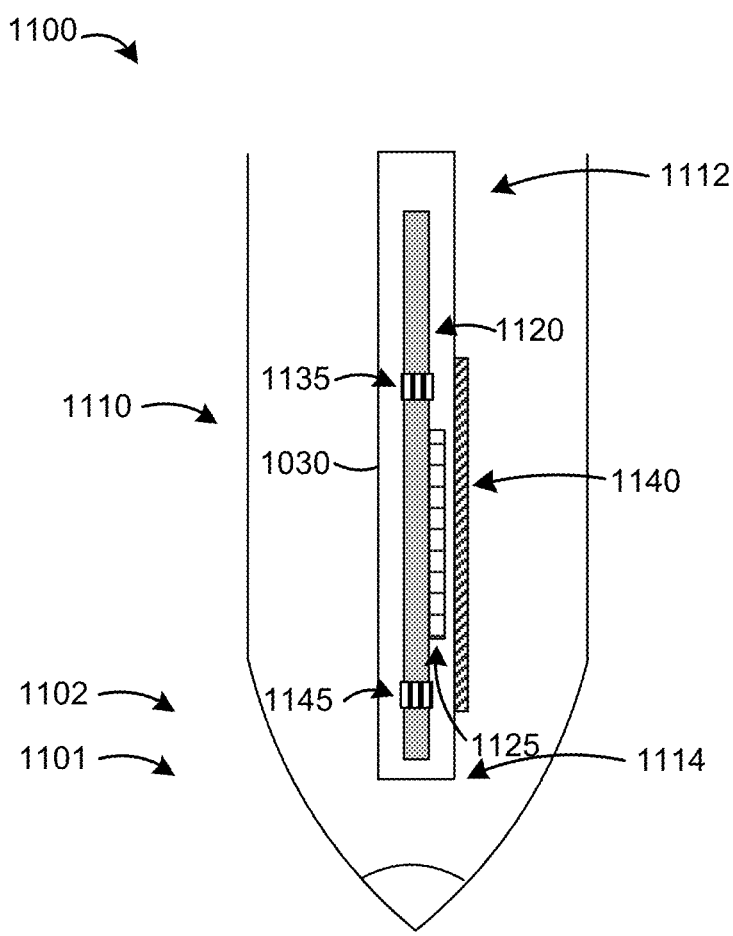
FIG. 11 illustrates a detailed view of the distal end of a shaft portion of a thermal therapy applicator according to one or more embodiments.

FIG. 11 illustrates a detailed view of distal end 1101 of shaft portion 1110 of thermal therapy applicator 1100 according to one or more embodiments. Proximal and distal fiducial markers 1135, 1145 are disposed in the shaft portion on either side of ultrasound transducers 1125. The proximal fiducial marker 1135 is preferably disposed near the ultrasound transducers 1125 on the proximal side thereof (i.e., between the ultrasound transducers 1125 and the proximal end 1112 of tube 1130). The distal fiducial marker 1145 is preferably disposed near the ultrasound transducers 1125 on the distal side thereof (i.e., between the ultrasound transducers 1125 and the distal end 1114 of tube 1130). Disposing the proximal and distal fiducial markers 1135, 1145 near the ultrasound transducers 1125 can improve accuracy since tube 1130 can bend during use in the patient (e.g., as a result of contacting the pubic bone).

The proximal and distal fiducial markers 1135, 1145 can be formed out of an MRI-compatible material that is at least partially opaque such that it is visible or detectable in MRI images. It is noted that the MRI image can have image distortion at the center of the image, which is preferably where the ultrasound transducers 1125 are placed during imaging. The fiducial markers 1135, 1145 can be formed from metals such as brass and/or gold, which form "dark" fiducial markers. In addition or in the alternative, the fiducial markers 1135, 1145 can be formed from a liquid such as water and/or animal or vegetable oils, and/or a semi-solid such as agarose or petroleum gels, each of which forms a "bright" fiducial marker. The foregoing bright fiducial markers can be doped with copper-sulfate, gadolinium or other minerals. In some embodiments, one or both of the fiducial markers 1135, 1145 includes a dark fiducial marker adjacent or proximal to a bright fiducial marker, which can enhance the visibility of the respective fiducial marker 1135, 1145. In some embodiments, proximal fiducial marker 1135 includes the proximal end 1112 of tube 1130, which can be formed out of or can comprise brass and thus forms a dark fiducial marker. The proximal fiducial marker 1135 can also include water in the acoustic window 1140, which forms a bright fiducial marker. Transducer support and assembly member 1120, including transducers 1125, is disposed in tube 1130. Shaft portion 1110 and/or tube 1130 can comprise a plastic material, a carbon composite material, and/or a non-magnetic metal (e.g., brass, aluminum, and/or titanium).

The proximal fiducial marker 1135 can comprise a hollow body that functions as a fiducial cavity, as discussed in more detail below. Alternatively, proximal fiducial marker 1135 can comprise one or more of the materials described above with respect to proximal fiducial marker 1135.

The fiducial markers 1135, 1145 can be detected (e.g., by a controller) during MRI scans. The controller can determine the position of thermal therapy applicator 1100 and transducers 1125 in the patient based on the positions of fiducial markers 1135, 1145. In addition or in the alternative, some or all of acoustic window 1140, which is generally viewable in MRI images, can be used as a fiducial marker(s). For example, the length of acoustic window 1140 can be used as a fiducial maker. In some embodiments, at least one of the length of acoustic window 1140 (as a fiducial marker) can be used in combination with at least one of proximal and/or distal fiducial markers 1135, 1145. The acoustic window 1140 can be an aperture or gap in tube 1130 that allows ultrasound energy to pass through.

In some embodiments, tube 1130 is segmented and a rigid, non-conductive material disposed between adjacent segments. The rigid, non-conductive material can disrupt current flow in the tube 1130. In some embodiments, tube 1130 is segmented, and each segment is separated by a gap. The gap provides insulation between adjacent segments to disrupt any current flow in tube 1130.

Figure 12:
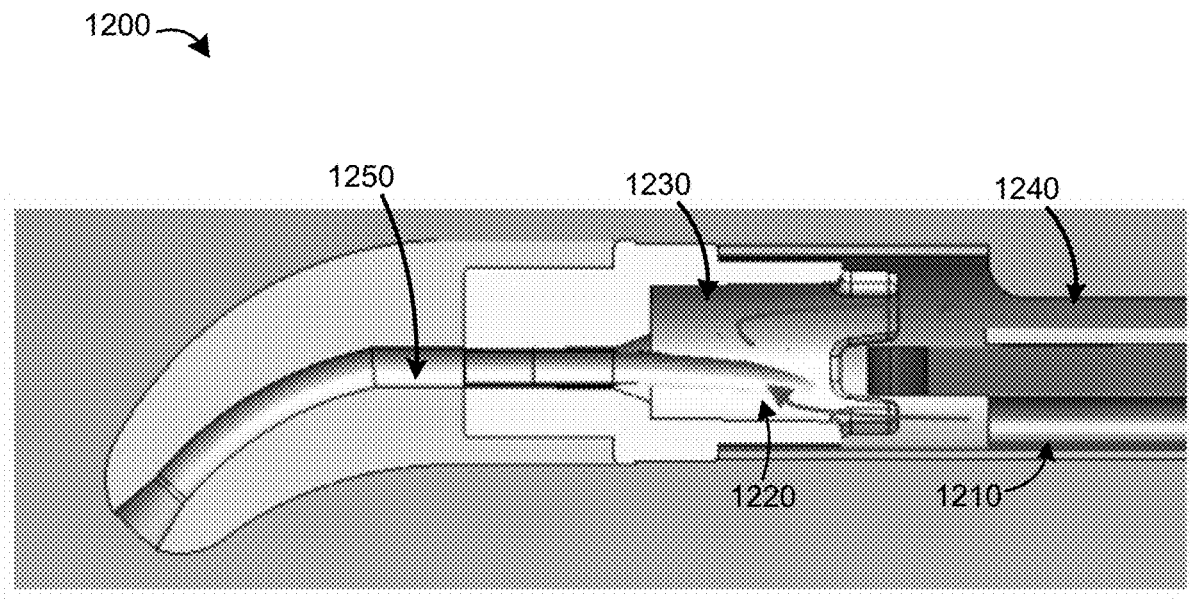
FIG. 12 is a block diagram of a tip of a thermal therapy applicator according to one or more embodiments.

FIG. 12 is a block diagram of a tip 1200 of a thermal therapy applicator according to one or more embodiments. The tip 1200 includes an inflow tube 1210 to introduce a cooling fluid (e.g., water) into an internal cavity or hollow body 1220 in tip 1100. The internal cavity 1220 forms a water pocket that functions as a fiducial cavity 1130. The fiducial cavity 1230 can be defined by internal walls of a body formed out of polyphenylsulfone (PPSU) with a silicone overmold. The water pocket appears as a bright fiducial marker while the surrounding material (i.e., PPSU and silicone) appear as a dark fiducial marker. The cooling fluid passes through the fiducial cavity 1230 and returns through water outflow conduit 1240. A tube 1250 for inserting a guidewire and/or for draining urine is illustrated in FIG. 12 for context.

Figure 13:
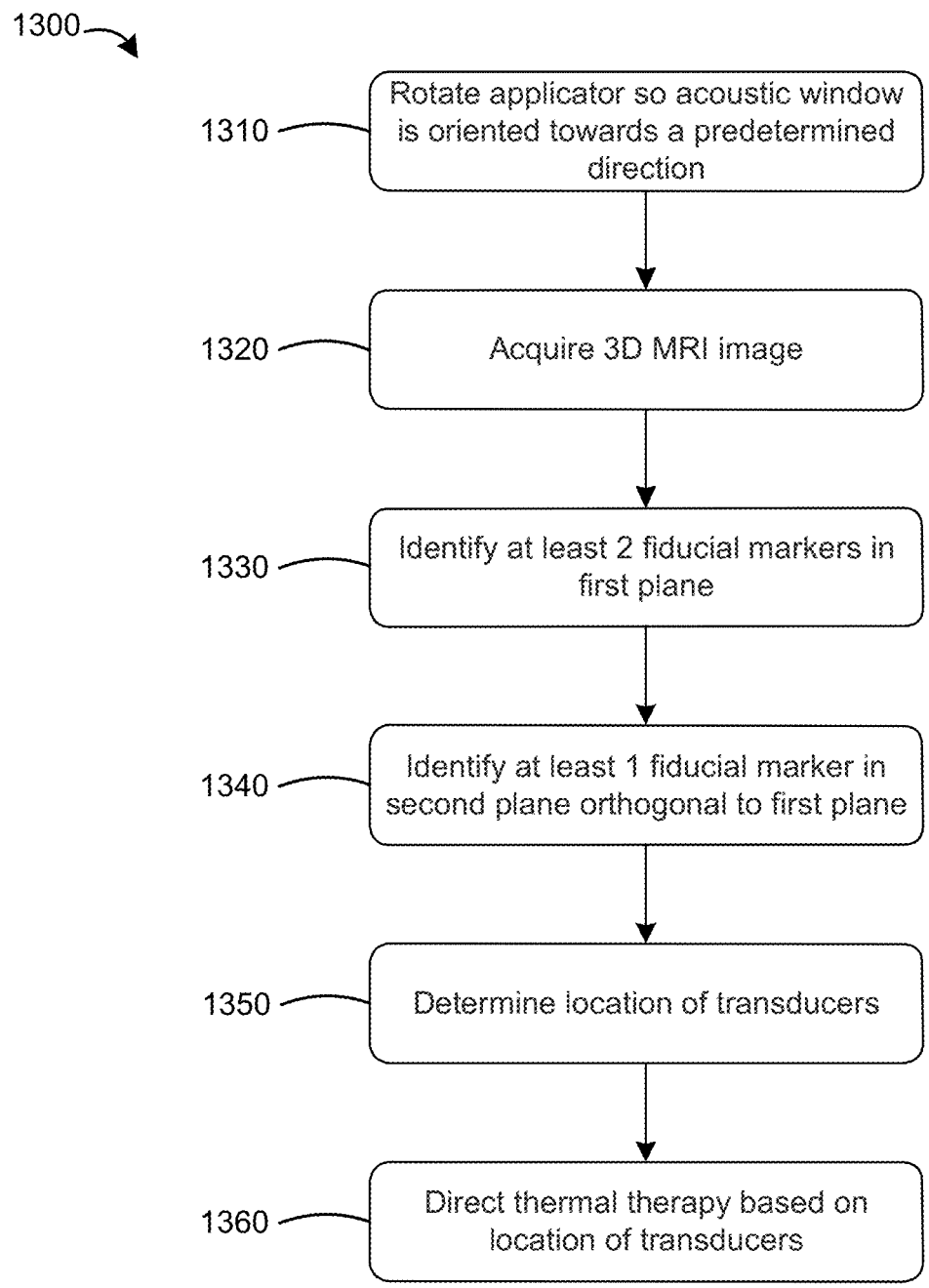
FIG. 13 is a flow chart of a method for determining the position of the transducers in a thermal therapy applicator disposed in a patient orifice, such as in a patient's urethra, according to one or more embodiments.

FIG. 13 is a flow chart 1300 of a method for determining the position of the transducers in a thermal therapy applicator disposed in a patient orifice, such as in a patient's urethra, according to one or more embodiments. The method is generally performed with a controller in communication with the thermal therapy applicator and an MRI machine. In step 1310, the controller causes the thermal therapy applicator to rotate such that the acoustic window is oriented towards a predetermined direction. For example, the acoustic window can be oriented towards the posterior of the subject. For example, when the subject is supine, the acoustic window would face "down" towards the patients back to be oriented towards the posterior of the subject. However, this is just an example and other orientations are within the scope of this disclosure. In step 1320, the controller causes the MRI machine to acquire a three-dimensional image of the patient including the thermal therapy applicator positioned according to step 1310. In step 1330, the controller or the operator (e.g., manually through a software user interface) identifies at least two fiducial markers in the first plane, such as the Sagittal plane. In some embodiments, the controller identifies the at least two fiducial markers through image processing. In other embodiments, the operator manually identifies the at least two fiducial markers (e.g., through a software user interface). The two fiducial markers can correspond to proximal and distal markers 1135, 1145, discussed above, which are disposed on opposing sides of the transducers. Alternatively, the two fiducial makers can correspond to (a) the proximal or distal fiducial marker 1135, 1145 and (b) the length of the acoustic window, the tube (e.g., tube 1130), and/or the shaft portion (e.g., shaft portion 1110). In step 1340, the controller identifies a fiducial marker on a second plane, the second plane orthogonal to the first plane. For example, the second plane can be the Coronal plane, though other planes orthogonal to the first plane are within the scope of this disclosure. When the at least two fiducial markers in step 1330 correspond to the proximal and distal markers 1135, 1145, the fiducial marker in step 1340 can correspond to the length of the acoustic window, the length of the tube, or the length of the shaft portion.

In step 1350, the controller determines the location of the transducers based on the known location of the fiducial markers with respect to the transducers. As discussed above, the shaft is secured to the handle by an adhesive or an attachment mechanism (e.g., bayonet lock mechanism 90), thus fixing the location of the transducers with respect to the fiducial markers. In 1360, the controller causes the thermal therapy applicator to direct a thermal therapy (i.e., ultrasound energy) to the subject based on the determined location of the ultrasound transducers.

Figure 14:
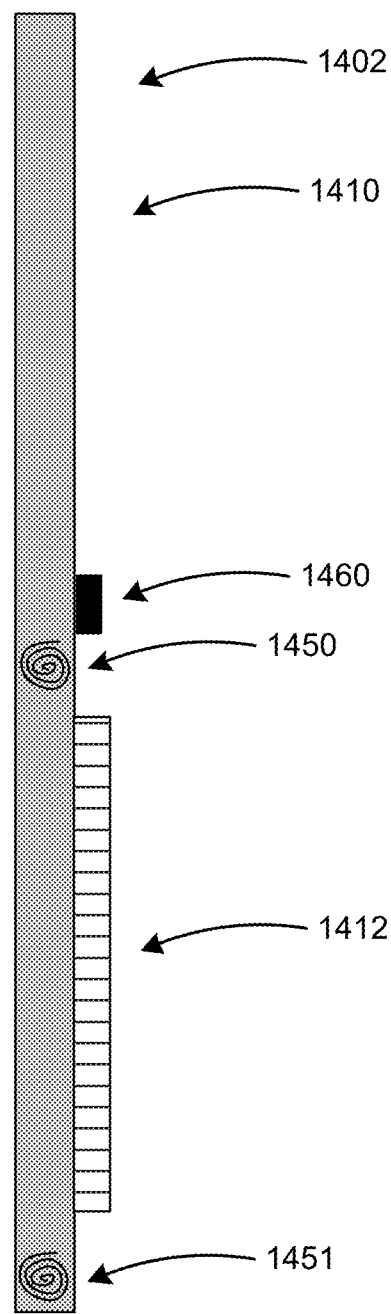
FIG. 14 illustrates a detailed view of transducer support and assembly member (e.g., PCB), including transducers, according to one or more embodiments.

FIG. 14 illustrates a detailed view of transducer support and assembly member (e.g., PCB) 1410, including transducers 1412, according to one or more embodiments. A pair of tracking coils 1450, 1451 is integrated or incorporated in the PCB of transducer support and assembly member 1410. The tracking coils 1450, 1451 are sensitive to the MRI signal generated in their immediate vicinity. An example of such a tracking coil is disclosed in U.S. Patent Application Publication No. 2015/0338477, titled "An Active Tracking System And Method For MRI," which is hereby incorporated by reference. A first tracking coil 1450 is disposed on the proximal side of transducers 1412 assembly and a second tracking coil 1451 is disposed on the distal side of transducers 1412 assembly. The controller can determine the position of the thermal therapy applicator in the patient based on the positions of tracking coils 1450, 1451, for example using 3 orthogonal gradient sequences.

In some embodiments, an inclinometer chip 1460 can be disposed on transducer support and assembly member 1410 proximal to transducers 1412 assembly. The inclinometer chip 1460 can determine the orientation or incline of the transducer support and assembly member 1410 and therefore the orientation or incline of transducers 1412 assembly. This can be useful, for example, when portions (e.g., elongated shaft portion) of the thermal therapy applicator is flexible to determine the actual orientation of the transducers 1412 assembly and corresponding ultrasound energy emitted therefrom. In some embodiments, the inclinometer chip 1460 can be a gyroscope or it can be MEMS-based. A controller can use the output signal from the inclinometer chip 1460 to determine the actual orientation of the transducers 1412 assembly and adjust the beam energy and/or phase accordingly such that the delivered ultrasound energy follows an ultrasound delivery plan.

In some embodiments, the thermal therapy applicator can include two or more of the foregoing position tracking systems and/or orientation tracking systems. For example, the thermal applicator can include the attachment features 835, bayonet lock mechanism 90, one or more fiducial markers (e.g., fiducial markers 1135, 1145, and/or the length of the acoustic window), one or more tracking coils 1450, 1451, and/or the inclinometer chip 1460, or any combination of the foregoing.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

We claim:

1. An apparatus for thermal therapy in a subject, comprising:
   an elongated cylindrical body having a first end thereof sized and configured for insertion into a male urethra;
   an array of ultrasonic sources disposed within said elongated cylindrical body and substantially arranged along an axis of said elongated cylindrical portion proximal to said first end of the elongated cylindrical portion, the ultrasonic sources being electrically driven to provide thermal therapy to said subject;
   a first fiducial marker disposed between said array of ultrasonic sources and said first end of said elongated cylindrical body;
   a second fiducial marker disposed between said array of ultrasonic sources and a second end of said elongated cylindrical body;
   a transition body portion directly connected to said second end of said elongated cylindrical body, said transition body portion including a flared portion that limits a depth of said insertion into said male urethra and a flanged portion, said flanged portion disposed between said second end and said flared portion;

an elongated printed circuit board disposed in said elongated cylindrical body and extending from said first end of said elongated cylindrical body to said transition body portion such that a portion of said elongated circuit board is disposed outside said depth of said insertion, said circuit board including a plurality of printed circuit lines respectively coupled to a plurality of said ultrasonic sources of said array, said circuit lines providing power and control signals to said respective plurality of ultrasonic sources and driving said sources to deliver acoustic emissions of respective frequency and power depending on the respective power and control signals, said plurality of circuit lines on said circuit board being electrically and mechanically coupled to said plurality of ultrasonic sources of said array by way of respective conducting epoxy points or pads of finite thickness so as to cause a gas-filled separation between back sides of said ultrasonic sources and said circuit board therefore so as to cause an outward radiation of ultrasonic energy from an outward face of said ultrasonic sources, wherein said epoxy points or pads are disposed between said ultrasonic sources and said circuit board, said gas-filled separation having a width determined by said thickness of said epoxy points or pads and a height determined by a distance between adjacent epoxy points or pads;

a rotational mechanical coupling directly connected to said flanged portion that supports and secures said elongated cylindrical portion, said rotational mechanical coupling further designed and arranged to permit mechanical rotation of said elongated cylindrical portion about said axis thereof and including a geared wheel configured to mechanically engage a rotational driver to convert a rotational movement of said driver to a corresponding rotational movement of said geared element; and at least one fluid conduit running through said rotational mechanical coupling permitting a fluid to circulate into and then out of said apparatus by flowing from said second end towards said first end of the elongated cylindrical portion and back again.

2. The apparatus of claim 1, wherein said first fiducial marker comprises a fiducial cavity.

3. The apparatus of claim 2, wherein said fiducial cavity comprises an internal cavity disposed in said elongated cylindrical body.

4. The apparatus of claim 1, wherein said second fiducial marker includes an acoustic window defined on said elongated cylindrical body.

5. The apparatus of claim 1, further comprising a complementary attachment mechanism comprising:

a female body member having apertures defined therein, said female body member disposed on a tube in the elongated cylindrical body, the elongated printed circuit board disposed partially in said tube; and a male body member having tabs that engage the apertures in the female body member, said male body member disposed on the transition body portion.

6. The apparatus of claim 5, wherein said female body member is tubular and said male body member is cylindrical.

7. The apparatus of claim 6, wherein each aperture includes a first portion that extends axially with said female body member and a second portion that extends circumferentially with respect to said female body member.

8. The apparatus of claim 7, wherein said second portion of a first aperture extends circumferentially in a first direction and said second portion of a second aperture extends circumferentially in a second direction, said second direction opposite to said first direction.

9. The apparatus of claim 1, further comprising a tube in the elongated cylindrical body, the elongated printed circuit board disposed partially in said tube, said comprising brass.

10. The apparatus of claim 9, wherein said tube is segmented and adjacent segments are separated by a gap, whereby the gap disrupts a current flow in said elongated cylindrical body.

11. The apparatus of claim 10, further comprising a rigid, non-conductive material disposed in each gap.

12. The apparatus of claim 1, further comprising an inclinometer chip disposed on said elongated printed circuit board proximal to said plurality of said ultrasonic sources.

13. The apparatus of claim 1, further comprising tracking coils integrated in said elongated printed circuit board.

14. The apparatus of claim 13, wherein a first tracking coil is disposed on a distal side of said ultrasonic sources and a second tracking coil is disposed on a proximal side of said ultrasonic sources.

* * * * *